United States Patent [19]

van der Stoel et al.

[11] Patent Number: 4,485,243

[45] Date of Patent: Nov. 27, 1984

[54] PROCESS FOR THE PREPARATION OF A 2-ALKYLPYRROLE

[75] Inventors: Roland E. van der Stoel, Buchten; Petrus H. J. Janssen, Geleen; Cornelis G. M. van de Moesdijk, Elsloo, all of Netherlands

[73] Assignee: Stamicarbon B.V., Geleen, Netherlands

[21] Appl. No.: 383,961

[22] Filed: Jun. 1, 1982

[30] Foreign Application Priority Data

Jun. 2, 1981 [NL] Netherlands ................ 8102656

[51] Int. Cl.$^3$ ............................................. C07D 291/04
[52] U.S. Cl. ..................................... 548/564; 548/565; 548/579
[58] Field of Search .................... 548/564, 565, 579

[56] References Cited

FOREIGN PATENT DOCUMENTS 699032 11/1940 Fed. Rep. of Germany ...... 548/564

OTHER PUBLICATIONS

Journal of Organic Chemistry, vol. 23, Sep. 1958, pp. 1281-1286, J. H. Burckhalter, et al.: "Synthesis of Nicotine Analogs".

Journal of the Chemical Society, 1948, pp. 186-188, E. B. Knott: "Beta-cycloylpropionitriles, Part III, Reduction to 2-cyclyl-delta2-pyrrolines . . . ".

Chemische Berichte, vol. 95, 1962, pp. 307-318, F. Korte, et al.: "Pyrrol- und Pyrrolidin-carbonsaure-(3-)-athyle ster durch Katalyt . . .".

Primary Examiner—Paul M. Coughlan, Jr.
Assistant Examiner—Cecilia Shen
Attorney, Agent, or Firm—Cushman, Darby & Cushman

[57] ABSTRACT

A process is described for the catalytic gas phase reduction of 4-oxoalkanenitriles to form 2-alkylpyrroles in high yields and conversions.

6 Claims, 3 Drawing Figures

PROCESS FOR THE PREPARATION OF A 2-ALKYLPYRROLE

This invention relates to a process for the preparation of 2-alkylpyrroles. Such compounds are important, among other things, for use in the paint industry and for the preparation of agricultural chemicals.

It is known in the art that 2-methylpyrrole can be formed by the liquid phase catalytic reduction of levulinic acid nitrile with hydrogen under high pressure at a yield of 10–20% (see the German patent Specification No. 699,032). However, this reduction process also forms the less desired 2-methylpyrrolidine at a yield which is actually higher than that of the 2-methylpyrrole. Thus, this known process is hardly suitable, for the practical production of 2-methylpyrrole because the yield is rather low and only a low proportion of the starting nitrile is actually converted to the desired product. Also, a very high hydrogen pressure must be applied.

It has now been found by the present invention that 2-methylpyrrole, and other 2-alkylpyrroles, can be readily prepared by a gas phase reduction in high yields and conversions, and while using a substantially lower hydrogen pressure, than in the case of said known process.

Figure 1:
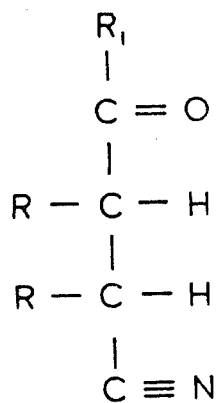

The process according to this invention for the preparation of a 2-alkylpyrrole involves starting with a 4-oxoalkanenitrile of the formula (FIG. 1)

Figure 2:
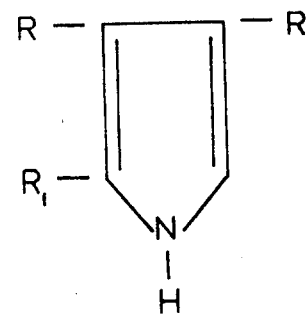

wherein $R_1$ represents an alkyl group of up to 3 carbon atoms and the two R groups independently represent hydrogen or an alkyl group of up to 2 carbon atoms. Such compound is reduced in the gas phase with hydrogen, in the presence of a catalyst containing a metal from group VIII or group Ib of the periodic table (or a compound of such a metal), with formation of a reaction mixture containing a 2-alkylpyrrole of the formula (FIG. 2)

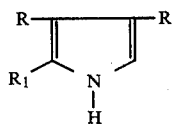

where $R_1$ and R have the meanings mentioned above.

If the starting compound is levulinic acid nitrile, 2-methylpyrrole is obtained. If, for instance, 2,3-dimethyl-4-oxopentanenitrile is taken as the starting compound, then 2,3,4-tri-methylpyrrole will be formed.

Advantageously a catalyst containing a metal or compound of a metal from the group of platinum, palladium and rhodium is used in this new process.

The catalysts can be employed on a solid, particulate supporting material, such as activated carbon, graphite, silicon oxide, zinc oxide, aluminum oxide, magnesium oxide and mixtures of these materials. Aluminum oxide is particularly suitable as the supporting material. A promotor can be added to the catalyst as well, such as an alkali metal. The amount of the catalyst on the carrier may usefully vary from 0.1 to 30 wt.% (calculated as metal and based on the total amount of catalyst material including the carrier).

The process according to this invention can be carried out at various temperatures, for instance a temperature of 150°–350° C., advantageously a temperature of between 175° and 300° C., is suitable.

The process according to this invention is generally carried out by techniques already known in the art, as such, for performing catalyst gas phase reactions, for instance by passing the gaseous starting material, diluted (if so desired) with an inert gas such as nitrogen, together with hydrogen, over the catalyst used in the form of a fixed bed and while applying a space velocity of between, for instance, 0.03 and 2 g starting material per ml catalyst (bulk volume) per hour. The bulk volume is the volume of the catalyst material after it has been subjected to vibration in order to approach a volume minimum.

The process according to this invention can be carried out with different quantities of hydrogen, for instance a quantity of 1–50 moles hydrogen per mole starting material. More than 50 moles hydrogen per mole starting product could be used, but this does not result in an advantage.

The pressure used in the process is not critical, and may conveniently vary from, say, 0.7 atmospheres up to 15 or 20 atmospheres, or more if desired. High pressures need not be used, and the process is usefully practiced between 1 and 5 atmospheres.

The 4-oxoalkanenitriles used in this process can be prepared as is known in the art, for instance by the reaction of hydrogen cyanide with an α-β-unsaturated ketone (see Methoden der Organischen Chemie HOUBEN-WEYL 8, pp. 272–274).

Figure 3:
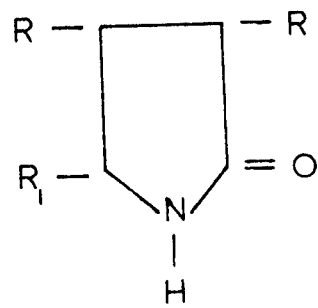

By cooling the gaseous reaction mixture obtained from this process of the invention a condensate can be separated from the hydrogen-containing gas, which latter can be recirculated to the process. In addition to the 2-alkylpyrrole, this condensate may contain a small quantity of the corresponding 5-alkylpyrrolidone-2 of the formula (FIG. 3)

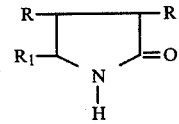

where $R_1$ and R have the meanings mentioned earlier. For instance, from levulinic acid nitrile the 5-methyl-pyrrolidone-2 may be formed. The condensate obtained can be further separated by, for instance, fractional distillation.

In the following illustrative, but non-limiting examples will further elucidate the invention.

Example I

Through a vertical tubular reactor (18 mm diameter, 400 mm length) containing a zone of 25 ml (bulk volume) catalyst a vaporous mixture of levulinic acid nitrile and hydrogen (6 moles hydrogen per mole nitrile) is passed from top to bottom at atmospheric pressure for 3.5 hours.

The catalyst column is bounded at the bottom by a zone of 10 ml and at the top by a zone of 100 ml of inert ceramic material. As catalyst, nickle on silica gel (10% by weight Ni, Houdry type H 1170, bulk density, determined by dividing the weight by the bulk volume, 0.6 g per ml) is used.

A vaporous mixture is obtained by evaporation of liquid levulinic acid nitrile, and the mixture of the vapor with hydrogen at the rate of 0.2 g levulinic acid nitrile per ml (bulk volume) catalyst is passed through per hour. The temperature of the catalyst is maintained at 250° C. by means of heating jacket round the reactor.

The composition of the vaporous reaction product mixture obtained is determined by passing the mixture through a small vessel cooled down to 0° C. and analysing the condensate thus obtained by gas chromatograph. From this analysis and the weight of the levulinic acid nitrile passed over, the conversion of the nitrile and the respective yields of 2-methylpyrrole and 5-methylpyrrolidone-2 can be calculated.

Conversion is understood to mean the quantity of levulinic acid nitrile converted (total quantity of nitrile passed over the catalyst, decreased by the quantity of nitrile in the condensate), expressed as a percentage of the quantity of nitrile passed over.

The yield of 2-methylpyrrole, or respectively of 5-methylpyrrolidone-2, is understood to mean the quantity of 2-methylpyrrole, or 5-methylpyrrolidone-2, in the condensate expressed as percentages of the quantity of 2-methylpyrrole, or 5-methylpyrrolidone-2, which can theoretically be formed from the quantity of nitrile converted.

The conversion in this example amounts to 98.9%. The yield of 2-methylpyrrole is 61.5% and of 5-methylpyrrolidone-2 is 2.9%.

Example II

Example I is repeated, using palladium and sodium on γ-aluminum oxide (0.5% by weight Pd and 0.4% by weight Na) as catalyst. Now, the conversion amounts to 95.5%. The yield of 2-methylpyrrole is 78.8% and of 5-methylpyrrolidone-2 is 13.4%.

Example III

Example I is repeated, using copper oxide on zinc oxide and γ-aluminum oxide (30% by weight CuO, 55% by weight ZnO) as catalyst. A conversion of 63.5% is reached. The yield of 2-methylpyrrole is 29% and of 5-methylpyrrolidone-2 is 21.6%.

Example IV

Example I is repeated, using 2.3-dimethyl-4-oxopentanenitrile as starting compound and using palladium and sodium on γ-aluminum oxide (0.5% by weight Pd and 0.4% by weight Na) as catalyst. The conversion now amounts to 91.5%. The yield of 2,3,4-trimethylpyrrole amounts to 61.3% and of 3,4,5-trimethylpyrrolidone-2 is 7.5%.

From the foregoing examples it will be seen that by this invention an efficient conversion of the nitrile starting material to the desired pyrrole product is achieved with only minimized production of pyrrolidone, or other, by-products.

What is claimed is:

1. A process for the preparation of a 2-alkylpyrrole from a 4-oxoalkanenitrile of the formula

wherein $R_1$ represents an alkyl group with 1–3 carbon atoms and the two R groups independently represent hydrogen or an alkyl group with 1–2 carbon atoms, which comprises contacting said nitrile at a temperature from 150° to 350° C., in the gas phase and in the presence of hydrogen with a catalyst containing a metal from group VIII or group Ib of the periodic system of elements whereby a reaction mixture is formed containing a 2-alkylpyrrole of the formula

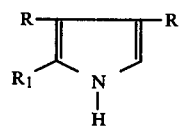

wherein $R_1$ and R have same meaning stated above.

2. Process according to claim 1, wherein said catalyst contains a metal from the group of platinum, palladium and rhodium.

3. Process according to either claim 1 or 2, wherein said catalyst is used on aluminum oxide as support.

4. Process according to claim 1 wherein said catalyst contains an alkali metal as a promoter.

5. Process according to claim 1 wherein said temperature is between 175° and 300° C.

6. Process according to claim 1 wherein 1–50 moles hydrogen is used per mole of said nitrile.

* * * * *